(12) United States Patent
Michelson

(10) Patent No.: US 6,692,501 B2
(45) Date of Patent: Feb. 17, 2004

(54) SPINAL INTERSPACE SHAPER

(76) Inventor: Gary K. Michelson, 438 Sherman Canal, Venice, CA (US) 90291

( * ) Notice: Subject to any disclaimer, the term of this patent is extended or adjusted under 35 U.S.C. 154(b) by 49 days.

(21) Appl. No.: 09/972,560

(22) Filed: Oct. 6, 2001

(65) Prior Publication Data

US 2002/0058944 A1 May 16, 2002

Related U.S. Application Data

(60) Provisional application No. 60/255,463, filed on Dec. 14, 2000, and provisional application No. 60/238,255, filed on Oct. 5, 2000.

(51) Int. Cl.[7] .............................................. A61B 17/14
(52) U.S. Cl. .......................................... 606/80; 606/79
(58) Field of Search .............................. 606/61, 79, 80, 606/82, 85, 96, 167, 170–172, 176–178, 180; 623/17.11–17.16

(56) References Cited

U.S. PATENT DOCUMENTS

| | | |
|---|---|---|
| 3,937,222 A | 2/1976 | Banko |
| 4,842,578 A | 6/1989 | Johnson et al. |
| 5,387,215 A | 2/1995 | Fisher |
| 5,601,556 A | 2/1997 | Pisharodi |
| 5,853,415 A | 12/1998 | Bertin et al. |
| 5,904,687 A | 5/1999 | Del Rio et al. |
| 6,063,088 A | * 5/2000 | Winslow ...................... 606/61 |
| 6,083,228 A | * 7/2000 | Michelson ................... 606/79 |

FOREIGN PATENT DOCUMENTS

WO     WO 99/63891     12/1999

* cited by examiner

*Primary Examiner*—Michael J. Milano
*Assistant Examiner*—D. Jacob Davis
(74) *Attorney, Agent, or Firm*—Martin & Ferraro, LLP

(57) ABSTRACT

A device and method for use in a vertebral spine to prepare a space between adjacent vertebral bodies to receive an implant. The device includes a shaft, and a mounting member at one end of the shaft. A working end is mounted on the mounting member and is coupled to a drive mechanism adjacent to the working end. The drive mechanism is operable to move the upper and lower cutters of the working end to create surfaces having predetermined contours in the end plate region of the adjacent vertebral bodies. A guard provides protected access to the disc space and the adjacent vertebral bodies for the working end of the bone removal device through a passageway.

39 Claims, 9 Drawing Sheets

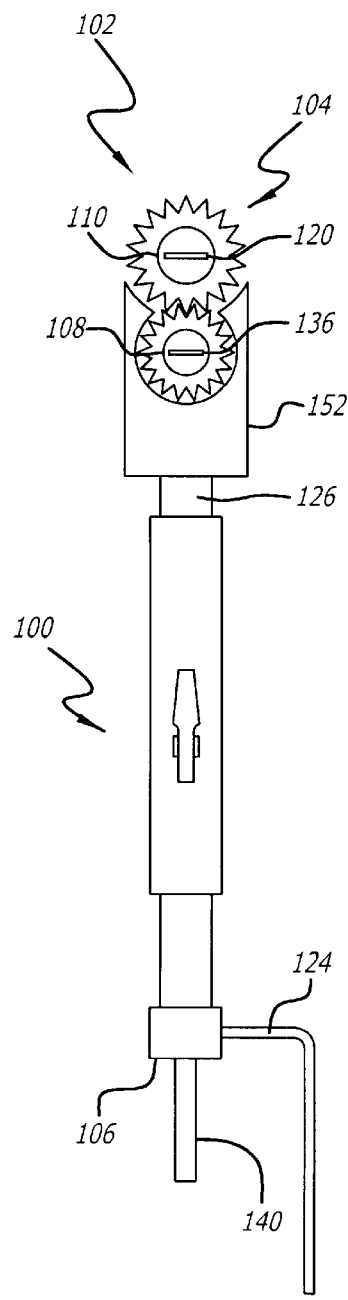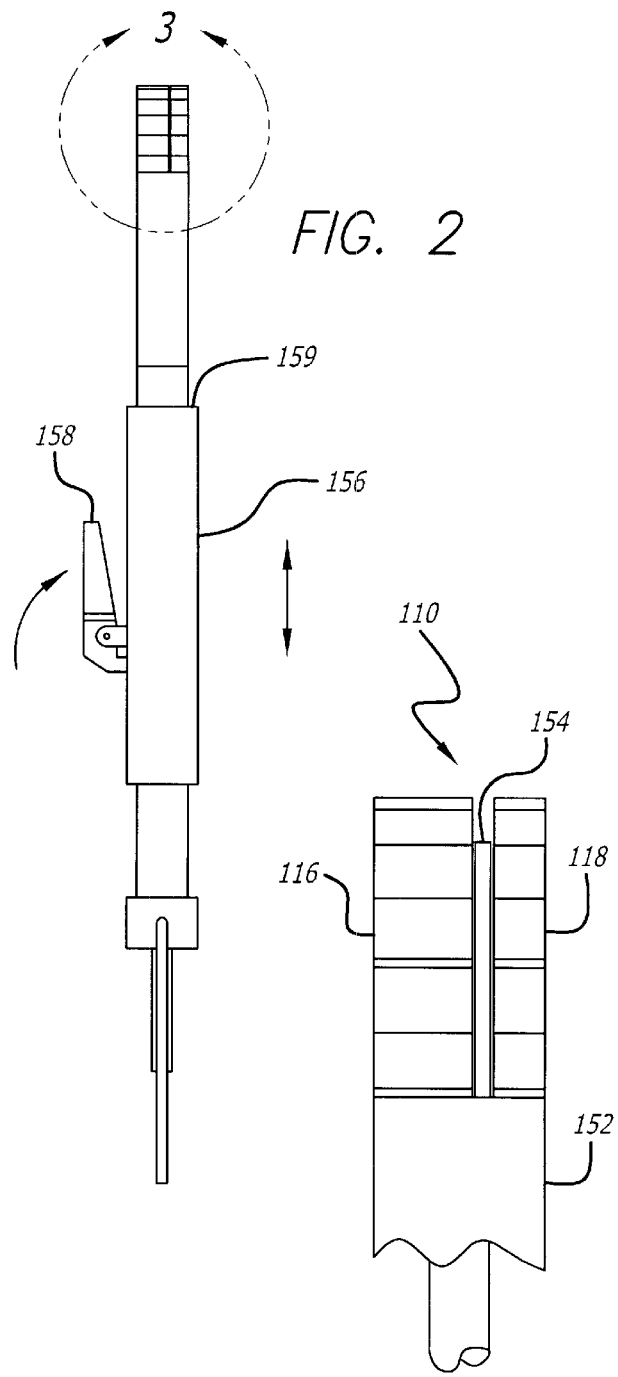
FIG. 1B
FIG. 2
FIG. 3

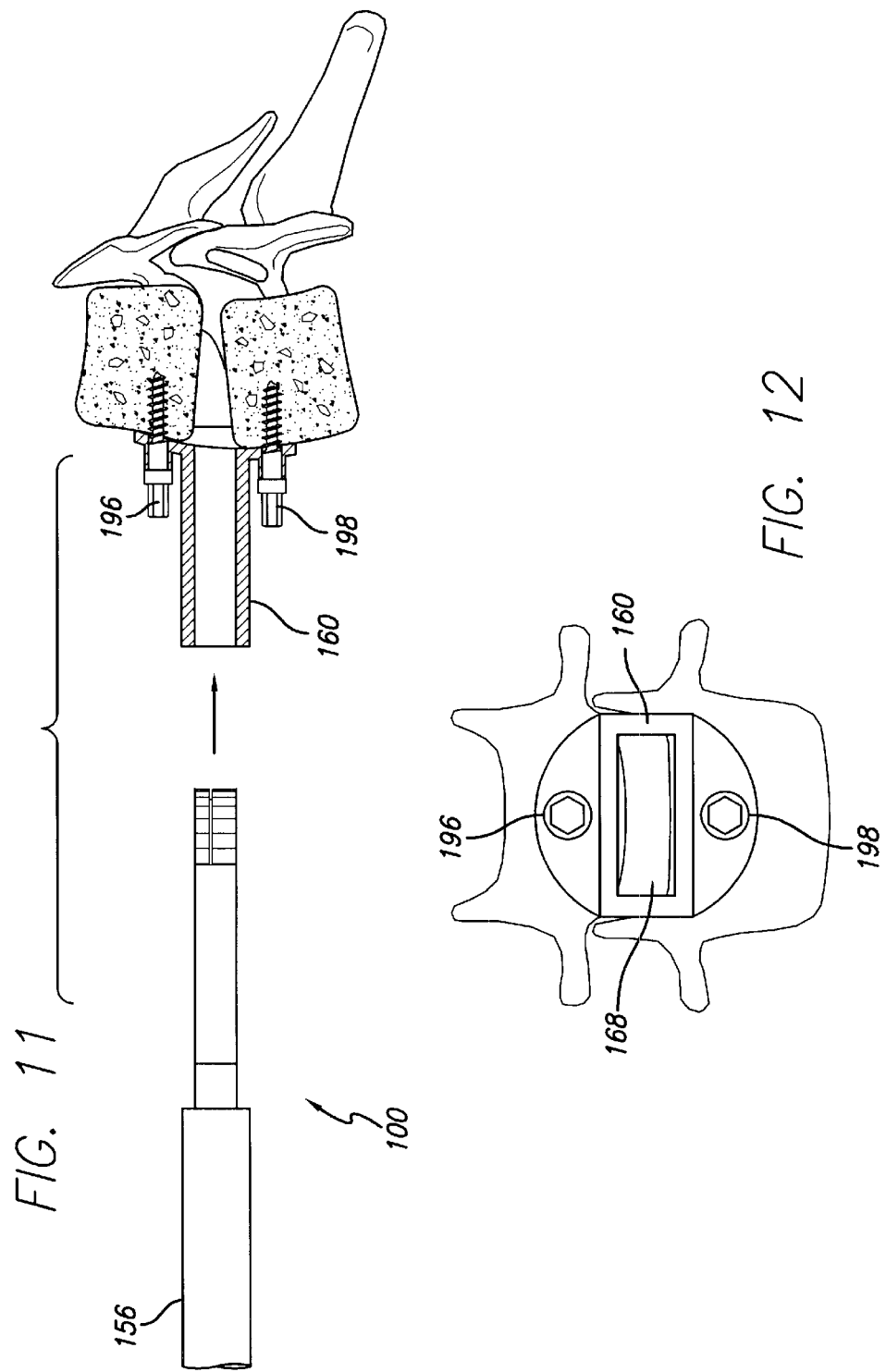

SPINAL INTERSPACE SHAPER

RELATED APPLICATIONS

This application claims priority to application Ser. No. 60/238,255, filed Oct. 5, 2000, and application Ser. No. 60/255,463 filed Dec. 14, 2000, both incorporated by reference herein.

BACKGROUND

Present methods of forming an implantation space between adjacent vertebral bodies in the human spine generally include the use of one or more of the following: hand held biting and grasping instruments known as rongeurs; curettes; drills and drill guides; rotating burrs driven by a motor; and osteotomes and chisels. Sometimes the vertebral end plate must be sacrificed as occurs when a drill is used to drill across the disc space and deeper into the vertebral bodies than the thickness of the bony end plate region. Such a surgical procedure necessarily results in the loss of the hardest and strongest bone tissue of the vertebral bodies located in the bony end plate region and thereby removes from the vertebral bodies that portion of its structure best suited to absorbing and supporting the loads placed on those vertebral bodies by an interbody spinal implant. Nevertheless, the surgeon must work upon the adjacent end plates of the adjacent vertebral bodies to access the underlying vascular bone that is capable of participating in the fusion by allowing active bone growth, and also to attempt to obtain an appropriately shaped surface in the vertebral bodies to receive the implant. Because the end plates of the adjacent vertebral bodies are not flat, but rather have a compound curved shape, and because the implants, whether made of bone or any other suitable implant material, when fabricated or manufactured, tend to have a geometric rather than a biologic shape, it is generally necessary to conform at least a portion of the vertebral bodies to the shape of the implant to be received therebetween.

It is important in forming the space between the adjacent bone structures to provide a surface contour that closely matches the contour of the implants so as to provide an adequate support surface across which the load transfer between the adjacent bone structures can be evenly applied. In instances where the surgeon has not been able to form the appropriately shaped space for receiving the implants, those implants may slip or be forcefully ejected from the space between the adjacent vertebral bodies, or lacking broad contact between the implant and the vertebral bodies, a failure to obtain fusion may occur.

Prior devices having a plurality of rotating cutting elements for removing bone with a drive mechanism between the cutting elements had limitations in certain applications. For example, if the bone to be cut was thicker than the individual thickness of each of the cutting elements, then the portion of the device between the cutting elements could hit the uncut bone and stop the bone removal device from advancing deeper into the bone being cut. Further, the presence of the drive member between the cutting elements kept the cutting elements spaced apart and thus could prevent the placement of the bone removal device into very narrow spaces such as, but not limited to, disc spaces as might be found in some instances in the cervical spine.

There remains therefore a need for an improved spinal interspace shaper that does not have such limitations so as to achieve the desired purposes as described herein.

SUMMARY OF THE INVENTION

The present invention relates to a bone removal device for insertion into and at least in part across the height of a disc space between adjacent vertebral bodies in the human spine, and a guard for providing protected access to the disc space and for maintaining a desired positioning of the adjacent vertebral bodies relative to each other, and to a method of working on those portions of the vertebral bodies adjacent that disc space to remove bone material sufficient to form a desired contoured end plate and to thereby access the underlying vascular bone. For purposes of this application, the bony "end plate region" of the vertebral bodies is defined as the outer shell of compact bone (the bony end plate) adjacent to the spinal disc and the underlying subchondral zone.

The apparatus and associated method of the present invention is adapted to form a surface on or into each of the vertebral body surfaces that are adjacent the intervertebral disc space. The prepared spaces are formed through the inert outer bone of the vertebral bodies to get to the vascularized underlying bone, preferably, without generally removing all of the thickness of the end plate region. The formed surface (s) have a defined shape and a contour corresponding to a preferred interbody spinal implant to be implanted in the disc space.

The bone removal device of the present invention is useful in the cervical, thoracic, and lumbar spine from anterior to the transverse processes of the vertebrae, lateral or anterolateral in the thoracic and lumbar spines, or from posterior in the lumbar spine. The bone removal device, in a preferred embodiment, generally includes a cutting element movably and preferably replaceably mounted on the distal end of a shaft. A depth limiting mechanism preferably controls the depth of insertion of the cutting element into the intervertebral space (i.e., the disc space). The device also includes a handle that may be detachable from the shaft. As used herein, the term "handle" refers to a portion of the device that a surgeon may grip or otherwise manipulate to guide the working end of the device. That "handle" may in fact have multiple purposes. For example, the handle may be a portion of the shaft on which the working end is mounted at one end. Alternatively, the handle may be part of a segment that connects the device to a power source. For example, the handle may be part of a power source that supplies pressurized gas to the power source if turbine driven, or the handle may be a drill, but the term "handle" is used herein in its broadest context to refer to that which the surgeon grasps to use the present invention.

Additionally, the shaft may be detachable from the working end. The device also includes a drive mechanism that transmits power to activate, i.e., move, the cutters. The drive mechanism connects to an energy source, e.g., a rechargeable battery that further may be but need not be housed within the handle of the device. By way of example only, the drive mechanism may include an electric motor or an electromagnetic oscillating mechanism. Or, again by way of example only, the drive mechanism and handle in which it may be disposed may include the head unit of a gas powered turbine of a type commonly used in other surgical instruments.

In a preferred embodiment, the working end is generally as wide as the spinal implant to be implanted or the width of a combined plurality of implants adapted for side-by-side use between the adjacent vertebral bodies adjacent the disc space. The receiving bed, i.e., the prepared surface of the vertebral bodies, when formed by the device, will correspond in shape, size, and contour to the corresponding surfaces of a preferred spinal implant or combined width of implants to be implanted. The surface produced by the bone removal device is generally flat or concave to correspond to the upper or lower vertebral body contacting surfaces of the implant that will be implanted between the vertebral bodies. In an embodiment of the present invention having domed or convex upper and lower cutters or cutting members the device may be inserted into the spine and then turned on to form to desired shape into the adjacent vertebral bodies. The cutters have a leading end that is capable of cutting through bone and/or disc material to form a pocket or socket having a contour corresponding to the forward aspect of the leading end, as well as at least a portion of the side surfaces of the preferred implant to be implanted. These sidewalls assist in restraining the implant from lateral movement.

The working end of the present invention includes a pair of opposed, outwardly facing cutters which lie in planes that may be either parallel to each other or, alternatively, convergent to each other. The present invention saves time by simultaneously preparing both of the vertebral end plates adjacent a disc space. The bone removal device shapes the three-dimensional space created between the adjacent vertebral bodies, which space can be made to conform to the desired lordosis of that portion of the spine that will receive the implant. The end plate space may be, but need not be, identical to the height of the implant, as the implant may be there to optimize the distance of the disc space.

The drive mechanism of the bone removal device is preferably located adjacent the working end of the instrument permitting a reduction in the overall height of the cutting elements. This configuration permits the overall height of the cuffing mechanism to be thicker or given the same height, it can be less than what was previously possible with the cutting elements having a drive member therebetween because the cutting elements can be placed closer together. A reduced overall height of the cutting mechanism permits the placement of the bone removal device into narrower spaces, such as but not limited to disc spaces as might be found in some instances in the cervical spine, than previously possible. Moreover, because the space between the cuffing elements is minimized, the thickness of the cuffing elements may be increased.

The cutting element of the present invention is not limited to being a unitary, one-piece construction, regardless of the number of cutting surfaces of the cutting element. The cutting element may include multiple pieces that, by way of example and not limitation, are mountable on the end of the device to, in combination, define the overall shape of the cutting element and its surfaces. Thus, the term "cutting element" is used herein to refer to both a unitary, one-piece construction or a multi-piece construction.

The cutting element is preferably mounted on the mounting member and may be removable and interchangeable. In such an embodiment, the mounting member may be, but does not have to be, attachable to a shaft that is attachable to the handle. The cutting element and the mounting member may be separable from each other. Alternatively, the working end and the mounting member may, together, be removable from the handle.

While a preferred embodiment of the present invention is discussed and disclosed herein for creating a space between adjacent vertebral bodies in the spine, the present invention is not limited to a device for creating a space between adjacent vertebral bodies, but can also be used in other portions of the body where it is desirable to place an implant between adjacent bone structures. Furthermore, an embodiment of the present invention may have upper and lower cutting surfaces that are in angular relationship to each other so as to, for example, match the natural lordotic curvature of the human spine at the location of the vertebral bodies to be operated upon. Additionally, sequentially larger, that is wider and/or thicker, ones of the cutting elements, or mounting member, may be used to form the desired sized space in a step-wise fashion, or the working end may be sized to substantially match the final desired width of the surface to be formed in the vertebral end plate. Furthermore, the working end is preferably configured with a sharpened leading edge to allow the working end to "forward cut" as it is inserted between the adjacent vertebral bodies. In this manner, progressive insertion of the cutting element between the vertebral bodies is facilitated.

In a preferred embodiment, a guard for use with the bone removal device has a body with a passageway passing therethrough. In a preferred embodiment, a first disc penetrating extension and a second disc penetrating extension extend from the leading end of the guard and are adapted to be inserted into the disc space between adjacent vertebral bodies. The disc penetrating extensions are preferably adapted to distract and align the disc space, and restore lordosis. The disc penetrating extensions also further limit lateral excursion of the bone removal device and protect vital structures lateral to the disc space. In the alternative, the guard could be attached with screws or pins to each of the vertebral bodies like portions to bear upon the end plates.

The guard provides protected access to the disc space and the adjacent vertebral bodies for the working end of the bone removal device through a passageway, which may be sufficiently taller than the height of the space to be formed by the working end so as to allow for the sequential use of working ends of increasing height or the insertion of a spinal implant taller than the height of the working end thereby allowing the surgeon the option of keeping the guard in place after the cutting procedure. For example, the guard can be left in place distracting and aligning the adjacent vertebral bodies after the cutting step so that spacers (i.e. trial implants) can be trialed and then the implant of the optimal height, and perhaps of a greater height than the cutter, can be inserted.

The bone removal device preferably remains appropriately positioned relative to the height of the passageway during the cut. By way of example and not limitation, this may be achieved by having the bone removal device and guard aligned by a cooperative track, or a longitudinal groove and cooperating protrusion. In an alternative embodiment, a mounting element may be located between the cutting portion at the leading end of the bone removal device and the trailing end of the bone removal device. In a preferred embodiment, the mounting element can be taller than the cutting portion. When the taller mounting element passes through the passageway of the guard, it contacts the interior of the passageway to maintain the cutting portion in a preferred orientation to the guard so that the cutting portion can form an implantation space of a height less than the height of the passageway that is still properly positioned relative to removing the dense thickness of bone from each of the vertebral bodies adjacent the disc space being prepared. This height differential permits an implant having a height greater than the height of the implantation space to be inserted through the guard. Somewhere along the shaft an enlarged portion may cooperate with the inner height and even the rearward portion of a guard.

The leading end of the guard may have a foot plate adapted to contact the vertebral bodies when for use generally anteriorly or anteriorlaterally and may be contoured to generally conform to at least a portion of the exterior aspect of the vertebral bodies where contacted. The foot plate may have holes for receiving, for example, fasteners including spikes, bone screws, pins, prongs, nails, or the equivalent therethrough to secure the foot plate to the vertebral bodies or such spikes, bone screws, pins, prongs, or nails maybe part of the foot plate. The attachment of the guard with fasteners to the adjacent vertebral bodies may further secure the vertebral bodies in the desired relationship and hold the vertebral bodies steady for the cutting operation to be performed.

For use posteriorly, it is generally preferred that the guard have at least one and more preferably two disc penetrating extensions, such that a foot plate may be minimized or absent.

Thus, the present invention provides a device and method for preparing a disc space between adjacent vertebral bodies to receive a spinal implant, and prepares that disc space by removing a portion of the bony end plate region of those vertebrae adjacent that disc space to form predetermined surfaces in that vertebral bodies adjacent the disc space. The prepared spaces are formed through the inert outer bone of the vertebral bodies to get to the vascularized underlying bone, preferably, generally without removing the full thickness of bone in the end plate region. The prepared surfaces are sized and contoured to have broad intimate contact with the preferred spinal implant to be implanted between the adjacent vertebral bodies and along side walls of a socket, which broad contact provides for increased implant stability. This broad area of intimate contact between the vertebral bodies and the implant promotes bone ingrowth from the vertebral bodies into the implant, and also provides a broad area over which to support the incumbent loads so as to minimize the risk of vertebral collapse or subsidence of the implant into the vertebra.

While the present invention has been generally described above, and the preferred embodiments of that invention will be described in detail below, neither that general description nor the detailed description limits the scope of the present invention. That scope is defined by the claims appearing at the end of this patent specification.

OBJECTS OF THE PRESENT INVENTION

It is an object of certain embodiments of the present invention to provide a device and method for quickly, safely, effectively, and accurately working upon the region of the bony vertebral body end plate regions adjacent a disc space so as to, while preferably preserving bone of that region, to at least in part, remove bone such that to access the active bone growth end plate at least in part, remove bone to produce a socket to accept and implant corresponding in size, shape, and contour to an implant to be implanted between the adjacent vertebral bodies.

It is a further object of certain embodiments of the present invention, to provide a device capable of simultaneously working upon both of the vertebral body end plate regions adjacent a disc space to produce opposed receiving surfaces in the adjacent end plate regions corresponding in size, shape and contour to a preferred implant to be implanted, and in so doing to define the shape of the implant space.

It is a further object of certain embodiments of the present invention to provide a vertebral interspace preparation device that, in a preferred embodiment, is capable of working with linear insertion, i.e., insertion along a single axis, and without the need to substantially move the device from side to side within the disc space along a second axis. In such a preferred embodiment, the device has at a working end having a width generally corresponding to the width of the implant to be implanted, and a leading edge corresponding to a generally arcuate leading end of the implant to be implanted, for creating a space of a fixed geometry corresponding to an implant of corresponding dimensions.

It is a further object of certain embodiments of the present invention to have a safety mechanism built into the device that limits the depth of insertion of the device into the spine.

It is a further object of certain embodiments of the present invention to provide a vertebral interspace preparation device that can have interchangeable working ends so as to be capable of producing a variety of differently sized and contoured surfaces and shapes within the intervertebral space.

It is a further object of certain embodiments of the present invention to have cutters extending to the leading end of the device such that the device may remove bone along its leading end as it is advanced within the disc space.

These and other objectives of the present invention will occur to those of ordinary skill in the art based on the description of the preferred embodiments of the present invention described below. However, not all embodiments of the inventive features of the present invention need achieve all the objectives identified above, and the invention in its broadest aspects is not limited to the preferred embodiments described herein.

BRIEF DESCRIPTION OF THE DRAWINGS

FIG. 1B is a top plan view of a spinal interspace shaper bone removal device in accordance with one embodiment of the present invention;

FIG. 2 is a side elevation view of the bone removal device of FIG. 1B;

FIG. 3 is an enlarged fragmentary view along line 3 of FIG. 2;

FIG. 11 is a partial side sectional view of two adjacent vertebral bodies with the extended guard in partial cross-section installed into the disc space and secured to the adjacent vertebral bodies by installation screws with a bone removal device about to be inserted therein;

FIG. 12 is a trailing end view of the extended guard of FIG. 11 installed into the disc space and secured to the adjacent vertebral bodies by installation screws;

DETAILED DESCRIPTION OF THE DRAWINGS

The following description is intended to be representative only and not limiting. Many variations can be anticipated according to these teachings, which are included within the scope of the present invention. Reference will now be made in detail to a preferred embodiment of this invention, an example of which is illustrated in the accompanying drawings.

Figure 1A:
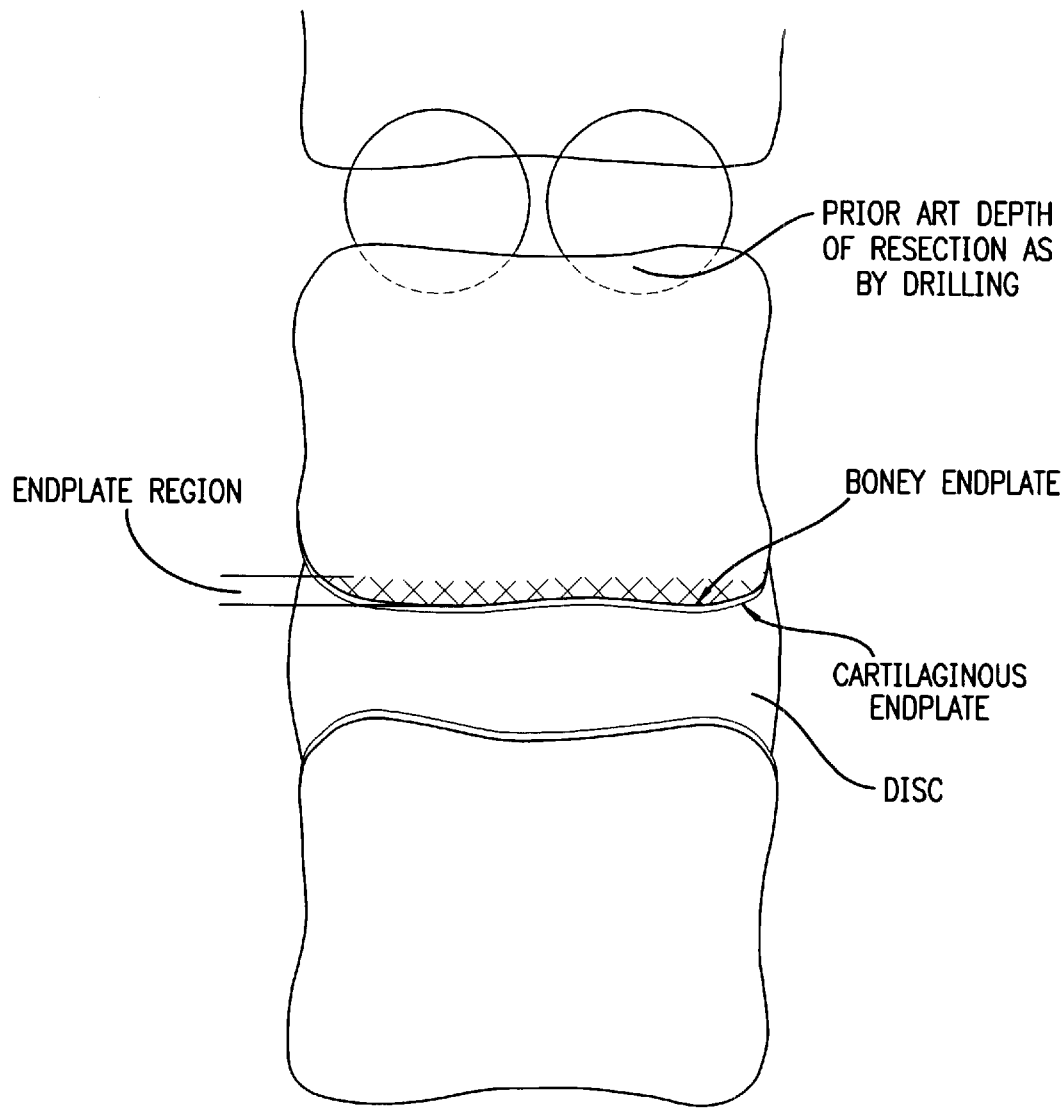
FIG. 1A is a front elevation view of two disc levels of the lumbar spine showing the prior art depth of resection resulting from drilling completely through the bony end plate region of adjacent vertebral bodies and showing the end plate region on a vertebral body.

Human vertebral bodies have a hard outer shell of compacted dense cancellous bone (sometimes referred to as the cortex) and a relatively softer, inner mass of cancellous bone. Just below the cortex adjacent the disc is a region of bone referred to herein as the "subchondral zone". As best shown in FIG. 1A, the outer shell of compact bone (the bony end plate) adjacent to the spinal disc and cartilaginous end plate and the underlying subchondral zone are together herein referred to as the bony "end plate region" and, for the purposes of this application, is hereby so defined. In the lumbar spine the thickness of the cortex end plate adjacent the disc space is generally not greater than several millimeters deep. By way of example, prior art threaded implants requiring approximately a 3 mm drill depth into the vertebral body and having threads of approximately 1 mm or more in height result in a total depth of penetration into the vertebral body of at least 4 mm sacrificing the best structural bone adjacent the disc space. The present instrumentation and method permits the preparation of the inter space to receive an implant with less depth of penetration into the vertebral bodies.

FIGS. 1B–4 show various views of bone removal device 100 in accordance with a preferred embodiment of the present invention. FIG. 1B is a top view of bone removal device 100 and FIG. 2 is a side view thereof. Bone removal device 100 has a leading end 102 including a cutting mechanism 104, and an opposite trailing end 106 configured to cooperatively engage a driving mechanism, such as a power drill, turbine, and the like, or an electrical driving mechanism suitable for the intended purpose. The particular power source that powers bone removal device 100 does not form a part of the present invention except to the extent it is adapted to achieve the appropriate and desirable amount of movement of the working end, or serves as part of the "handle" when in use.

Figure 4:
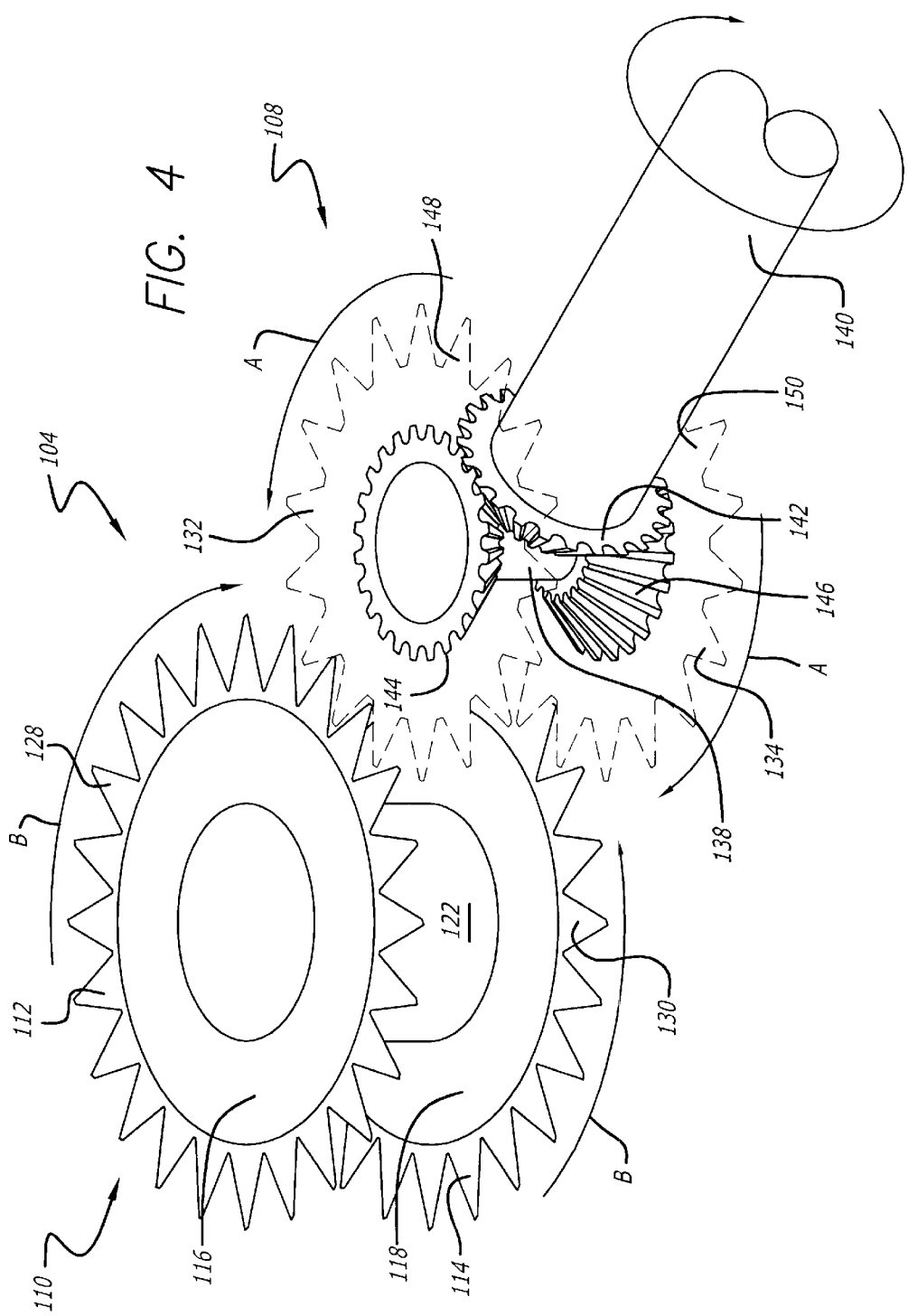
FIG. 4 is a detailed fragmentary view of the cutting portion and drive gears of the spinal interspace shaper bone removal device of FIG. 1B.

As shown in FIGS. 1B and 4, cutting mechanism 104 includes a drive element 108 and a working end 110. Working end 110 preferably includes two opposed cutters, upper cutter 112 and lower cutter 114 that are configured with a sharpened leading edge. In this embodiment, working end 110 preferably includes two disc-shaped cutting members 116, 118 that are removably mounted on the distal end of the device by a recessed connector 120 and connector shaft 122. Upper cutter 112 is formed on the edge of cutting member 116, and lower cutter 114 is formed on the edge of cutting member 118. Mounting member 152 facilitates removing cutting members 116, 118 and replacement with other disc-shaped members of similar or alternative cutting or abrading designs. Brace 124 prevents rotation of shaft 126 during use of the device such as by chucking shaft 26 into a drill and fitting brace 124 into a non-rotating portion of the drill.

In an alternative embodiment, cutters 112, 114 may be manufactured separately from cutting members 116, 118. For example, in FIG. 4, disposable or interchangable ring 128 includes upper cutter 112 and disposable or interchangable ring 130 includes lower cutter 114. Cutting ring 128 is mounted on cutting member 116, and cutting ring 130 is mounted on cutting member 118. Such a mounting may be accomplished by threadably connecting a cutting ring to its associated cutting member. The threads of such a threadable connection preferably oppose the direction of rotation of the cutting member when the device is in use. Other equivalent mountings to the threadable connection may be employed, such as where the ends of the wheel are configured such that one end secures into the other.

Drive element 108 is positioned to rotationally engage working end 110. Drive element 108 is preferably located adjacent to cutting members 116, 118. Drive element 108 preferably includes two disc-shaped drive members 132, 134 (shown in phantom in FIG. 4). Drive members 132, 134 may be removably mounted on bone removal device 100 by a connector 136 and connector shaft 138. Although two disc-shaped elements are preferred, it should be understood that a number of equivalent structures may be used to impart rotation to working end 110. For example, instead of two drive members 132, 134 as shown in FIG. 4, a hollow or solid cogwheel could be used to interface between working end 110 and a driving mechanism. Another alternative could employ the use of a threaded spindle acting as a drive element. Alternatively, a pulley, spindle, or other rotating device may be coupled to a power source to drive a cord, cable, or belt, or similar power-transferring element to thereby drive cutters 112, 114. Such an alternative embodiment removes the bulk of the drive mechanism from between cutters 112, 114 and is within the scope of the present invention. It is also possible and within the scope of the present invention to angle the cutting elements such that they converge towards leading end 102 to form an angled cut into the adjacent vertebral bodies.

Upper and lower cutting members 116, 118 and their associated cutters may rotate in opposite directions so as to mitigate any undesired torque and to avoid any tendency of the cutting end of the device to move laterally. This counter-rotating motion may be achieved by using a rotating drive rod 140 that extends through shaft 126 and is configured with a gear 142 at its distal end that engages with mating gear teeth 144, 146 formed on respective sides of drive members 132, 134. The resulting counter-rotation of drive members 132, 134 (shown by arrows A in FIG. 4) acts to counter rotate cutting members 116, 118 by way of cutting member engagement surfaces 148, 150, shown in FIG. 4 as radial teeth. This counter-rotating motion of members 116, 118 is illustrated by the arrows B in FIG. 4. Mating gear teeth 144, 146 may be inwardly sloping, ramped surfaces that engage cone-shaped gear 142 disposed on the distal end of a rotating drive rod 140 to turn drive members 132, 134 in opposite directions as drive rod 140 spins about its axis. Alternatively, cutting member engagement surfaces 148, 150, and driver 140 can be radially splined to engage one another or may comprise of any other known cord, cable, belt or similar power transferring element that operatively drives cutters 112, 114.

In the embodiment described, mounting element 152 may interchangeably receive various sizes of working end 110 and/or driving element 108. Thus, element 108 and/or working end 110 may be quickly and easily attached to and detached from mounting member 152 during surgery. In order to accommodate the various sizes of working ends and driving elements, mounting member 152 may be adapted to permit slidable adjustment between shafts 122 and 138. While in a preferred embodiment, upper and lower cutters 112, 114 are selected to have a width that is substantially the same as the width of the surface to be formed in the vertebral end plate, a surgeon might also elect to use a working end of lesser height than the ultimate desired depth of the surfaces to be formed. Thereafter, the surgeon may use a successively wider and/or taller work ends of the bone removal device until he arrives at the desired dimensions of the space formed between the adjacent bone structures.

The positioning of drive members 132, 134 adjacent to cutting members 116, 118, instead of between cutting members 116, 118, permits the overall thickness of cutting mechanism 104 to be less than was previously possible with cutting members 116, 118 having the bulk of a drive member therebetween because cutting members 116, 118 can be placed closer together. A reduced overall thickness of cutting mechanism 104 permits the placement of bone removal device 100 into narrower spaces, such as in narrow disc spaces for example, such as but not limited to disc spaces as might be found in some instances in the cervical spine, than was previously possible. Moreover, because the space between cutting members 116, 118 is reduced, the thickness of the cutting area may be increased to permit cutting thicker pieces of bone. For example, in prior devices where a relatively thick portion of the drive mechanism is located between the cutting members, if the bone to be cut is thicker than the individual thickness of each of the cutting members, then the portion of the device between the cutting members could hit the uncut bone and stop the bone removal device from advancing deeper into the bone being cut.

As shown in FIG. 3, in a preferred embodiment a thin portion 154 of mounting element 152 extends between cutting members 116, 118 to provide support and permit attachment of cutting members 116, 118 to mounting element 152. As shown in FIG. 2, a depth stop 156 having an end 159 for abutting a substrate to be cut, such as for example the exterior of a vertebral body, is in slideable engagement to mounting element 152 so as to adjust the depth of penetration of cutting mechanism 104 of bone removal device 100. An adjusting mechanism 158, such as a spring-biased lever for example, locks depth stop 156 at the depth selected by the surgeon. Depth stop 156 also may include an abutment surface or any number or shape of projection capable of carrying out the intended function and any known means for securing it. Adjustment mechanism 158 may also comprise a number of equivalent structures, such as, for example, one or more push button spring locks, adjustable turn screws, a collar with spring loaded detents or ball bearings and the like. Brace 124 extends from trailing end 106 for holding bone removal device 100 in a desired position relative to the drive means to which it attaches.

In another embodiment, mounting element 152 can be taller than cutting members 116, 118. When the taller mounting element 152 passes through the passageway of guard 160, it contacts the interior of the passageway to maintain the cutting mechanism 104 in a preferred orientation to guard 160 so that cutting mechanism 104 can form an implantation space of a height less than the height of the passageway. This height differential permits an implant having a height greater than the height of the implantation space to be inserted through guard 160.

As a further enhancement to the device it may have evacuation flutes for moving debris proximal. Additionally, an irrigation tube and/or a suction tube may be formed within, or outside of shaft 126. These irrigation and suction tubes may be connected to appropriate sources of irrigation fluid and a source of vacuum, respectively, to efficiently irrigate and clear the surgical site during use of the device.

Numerous other configurations of working end 110 are possible within the scope of the present invention. For example, upper and lower cutters 112, 114 may be convex to form concave receiving surfaces in the vertebral end plates. The geometry and configuration of the shapes of the upper and lower cutters and cutting members can be matched to the desired shape and configuration of the space which the surgeon intends to create between adjacent bone structures and to the desired contour of the surfaces created in the bone structures as is disclosed in applicant's International Patent Application No. PCT/US99/12890, filed Jun. 9, 1999, and applicant's U.S. Pat. No. 6,083,228, issued Jul. 4, 2000, both of which are incorporated herein by reference.

Additionally, working end 110 may be configured to have roughenings, knurls, ridges, small pyramid shaped projections, or any other surface configuration that is capable of cutting or abrading the bone structures.

Figure 5:
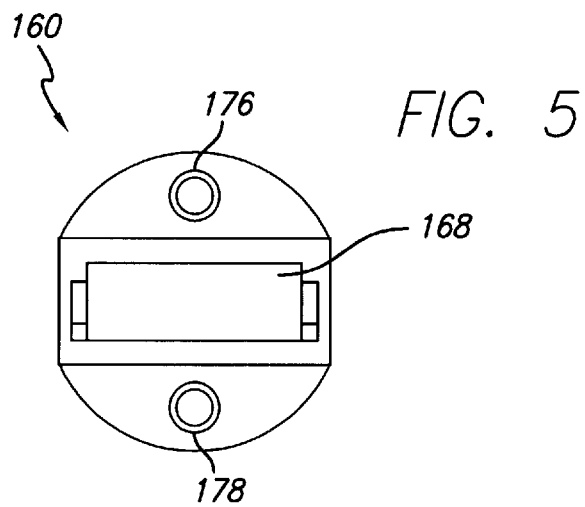
FIG. 5 is a trailing end view of an extended guard in accordance with one embodiment of the present invention.
Figure 6:
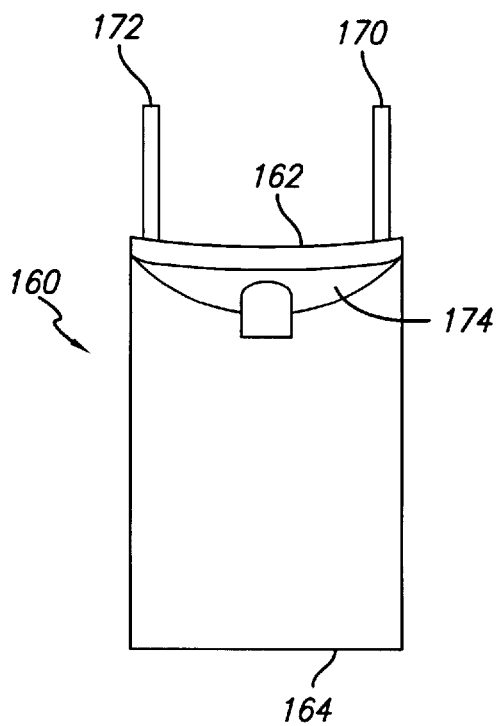
FIG. 6 is a top plan view of the extended guard of FIG. 5.
Figure 7:
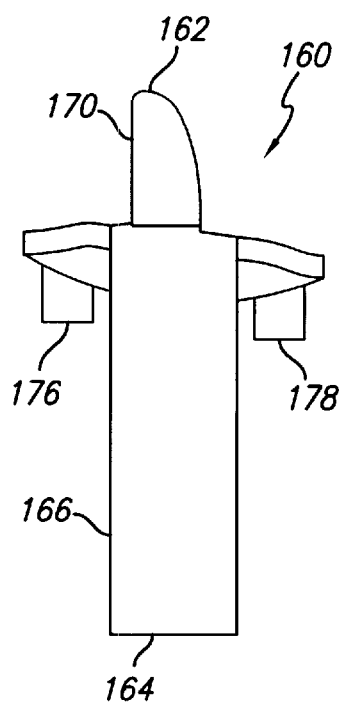
FIG. 7 is a side elevation view of the extended guard of FIG. 5.

FIGS. 5–7 show a guard 160 for use with device 100. In the preferred embodiment, guard 160 has a body 166 with a leading end 162, a trailing end 164 opposite leading end 162, and a passageway 168 passing therethrough. In a preferred embodiment, a first disc penetrating extension 170 and a second disc penetrating extension 172 extend from leading end 162. First disc penetrating extension 170 and second disc penetrating extension 172 are adapted to be inserted into the disc space between adjacent vertebral bodies. Guard 160 provides protected access to the disc space and the adjacent vertebral bodies for working end 110 through opening 168. Opening 168 is preferably taller than the height of working end 110. Such a taller opening 168 allows the sequential use of working ends 110 of increasing thickness or the insertion of a spinal implant taller than the thickness of working end 110 thereby allowing the surgeon the option of keeping guard 160 in place after the cutting operation. Additionally, body 166 may have a cross section transverse to its longitudinal axis with a complete or incomplete perimeter, (i.e. the cross section may be generally square, rectangular, oval, circular or any other shape with either an open or closed perimeter suitable for the intended purpose). The spinal implant is preferably sized and shaped to match the space formed in the spine by the working end.

Leading end 162 of guard 160 preferably has a foot plate 174 (for use anteriorly) adapted to contact the vertebral bodies and may be contoured to generally conform to at least a portion of the exterior aspect of the vertebral bodies in any or all planes. Foot plate 174 preferably is adapted to cover at least a portion of each of the two vertebral bodies adjacent the disc space into which guard 160 is to be inserted. Foot plate 174 may have receiving holes 176, 178 for receiving, for example, fasteners including spikes, bone screws 196, 198, pins, prongs, nails, or the equivalent therethrough to secure foot plate 174 to the vertebral bodies. The attachment of foot plate 174 with screws 196, 198 or the equivalent to the adjacent vertebral bodies may rigidly secure the vertebral bodies in the desired relationship and hold the vertebral bodies steady for the cutting operation to be performed, when the guard does not have disc penetrating extensions, or further secure it when it does. The disc penetrating extensions may be entirely sufficient by themselves such that no other means for securing the guard is needed. The example of the foot plate shown in FIGS. 5–8 is suitable for use in the anterior cervical spine. For use in the lumbar spine, preferably little or no foot plate would extend outward from the body of the guard, as the body of the guard itself functions as a depth limiting stop.

Guard 160 also may include one or more guide surfaces along the interior surface of passageway 168 to direct cutting mechanism 104 while accessing the disc space and adjacent vertebral bodies through passageway 168. Such guide surfaces may include any structure designed to direct the cutting mechanism. For example only, such structures can include a cooperative track, longitudinal groove, cooperating protrusion, and the like. However, it is emphasized that the guide surface may include any surface designed to direct cutting mechanism 104.

Figure 8:
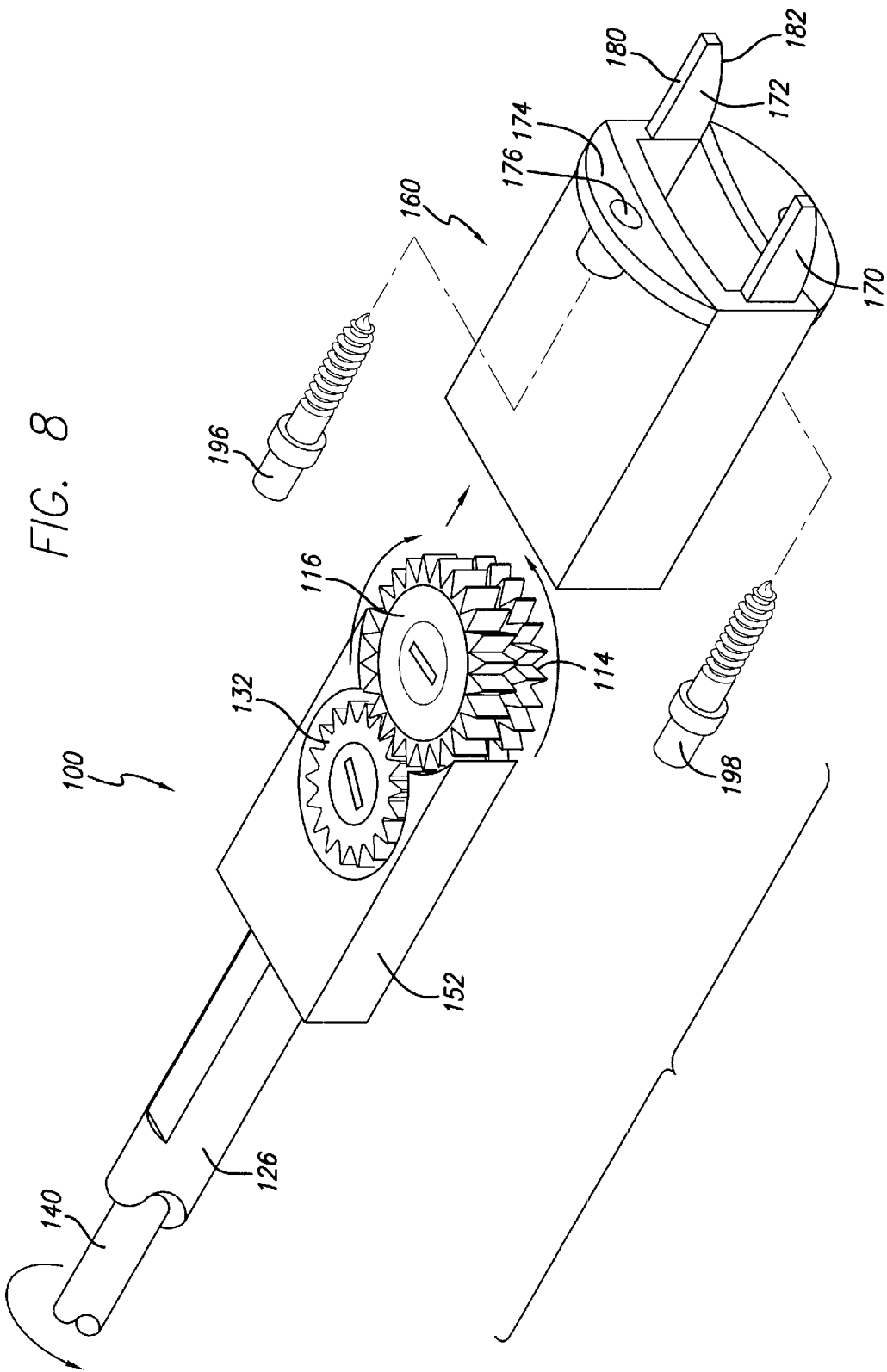
FIG. 8 is an exploded view of the bone removal device of FIG. 1B, extended guard, and installation screws in accordance with one embodiment of the present invention.

As shown in FIG. 8, first disc penetrating extension 170 and second disc penetrating extension 172 have an upper surface 180 and a lower surface 182 adapted to contact and support the end plates of the adjacent vertebral bodies. Upper and lower surfaces 180, 182 can be generally parallel to each other or can be in angular relationship to each other. One or both of upper and lower surfaces 180, 182 may be tapered proximate their insertion end to facilitate insertion of extensions 170, 172 into the disc space. An example of a configuration of extensions 170, 172 for use in the cervical spine that generally conforms to the bony architecture within the disc space is best shown in FIGS. 7 and 11. In the lumbar spine, for use from the posterior approach, extensions 170, 172 may have any configuration useful for the intended purpose including but not limited to those disclosed in applicant's U.S. Pat. No. 6,080,155 filed Feb. 27, 1995, incorporated herein by reference.

While not requisite, extensions 170, 172 are preferably adapted to distract and align the disc space, and to restore lordosis. Extensions 170, 172 further limit lateral excursion of bone removal device 100 and protect vital structures lateral to the disc space. Trailing end 164 of guard 160 cooperates with depth stop 156 of bone removal device 100 to limit the depth of penetration of cutting mechanism 104 into the disc space. Guard 160 assures balanced resection depth of each of the adjacent vertebral bodies and restrains migration of debris generated by the bone removal device. As best shown in FIG. 12, after guard 160 is properly positioned relative to the adjacent vertebral bodies, guard 160 provides the surgeon a line of sight through passageway 168 to evaluate the bone resection prior to actually performing it. As the length of the extensions 170, 172 are known to the surgeon and are appropriate for their intended purpose, the surgeon can, by direct observation, measurement, and/or x-ray, assess the appropriate depth for resection and implantation. Other shapes of disc penetrating extensions may be desired and are within the scope of the present invention.

Having described the apparatus, methods for its use will now be described. It should be understood that the order disclosed is only preferred and that the steps may be performed in other orders while still being within the scope of the present invention. Additionally, some steps may be repeated or omitted as necessary.

Figure 9:
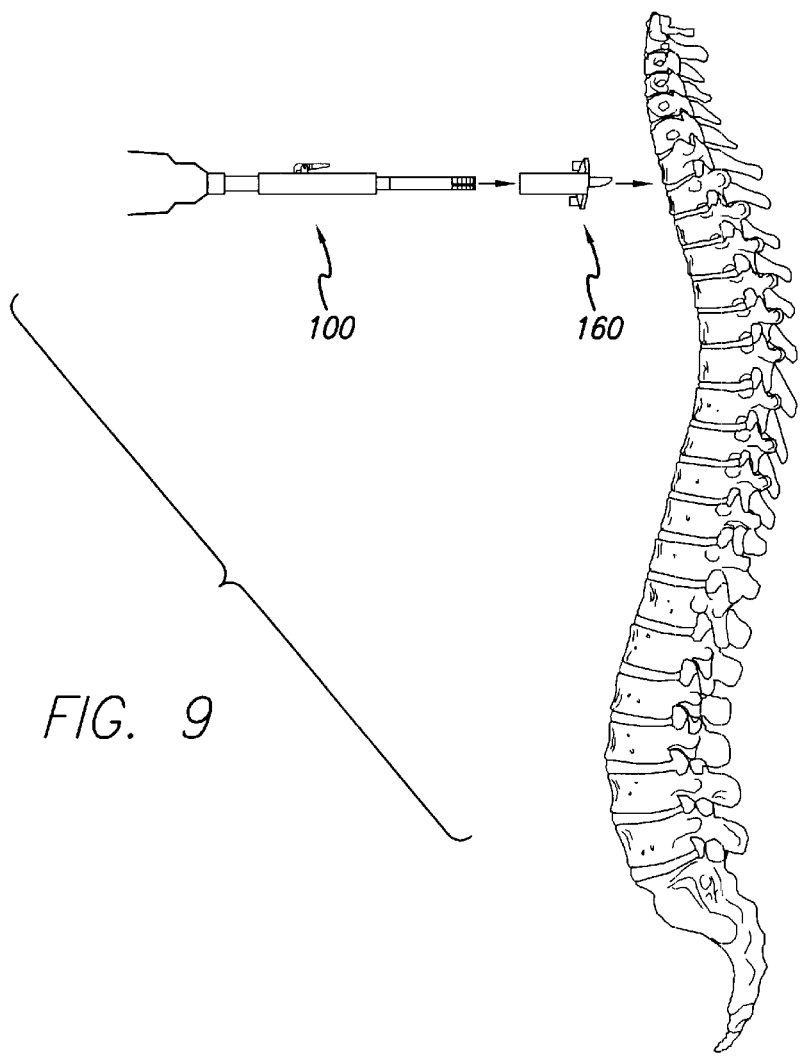
FIG. 9 is a side elevation view of a human spine with the instrumentation of FIG. 8 being used from an anterior approach to the spine.
Figure 10:
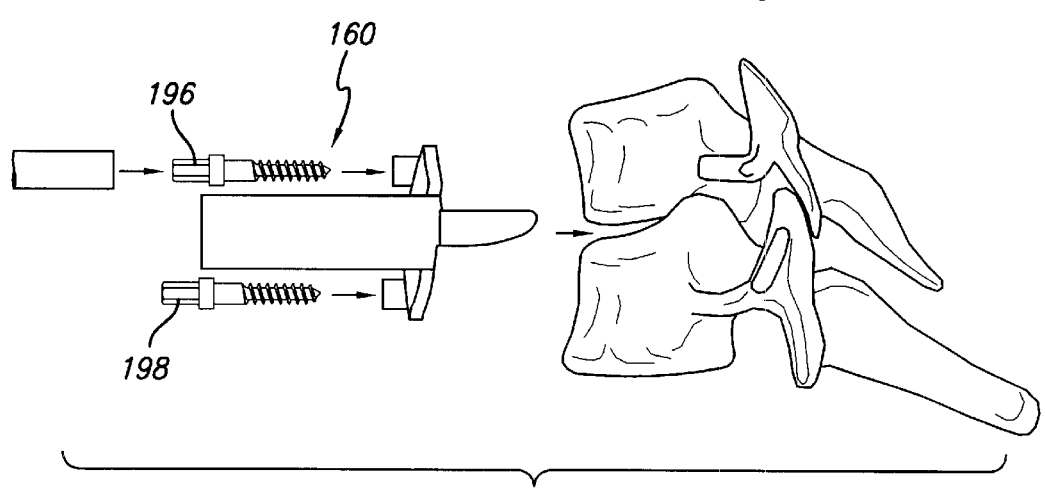
FIG. 10 is a side elevation view of the extended guard being installed from an anterior approach into the disc space between two adjacent vertebral bodies and being secured thereto by screws.

Referring to FIGS. 9–15, a method for use in the cervical spine from the anterior approach is described by way of example. As shown in FIG. 9, the correct disc space to be operated upon is identified by the surgeon by direct vision and counting, or preferably, by the use radiographical imaging with a marker. After the correct disc is identified, guard 160 is inserted into the disc space between the adjacent vertebral bodies as shown in FIG. 10.

The disc may have a portion excised and then guard member 160 is inserted such that extensions 170, 172 penetrate the disc space and contact the adjacent vertebral end plates adjacent that disc space. Guard insertion may be performed over a long distractor such as disclosed in applicant's U.S. Pat. No. 6,159,214, incorporated herein by reference. It is appreciated that guard 160 may be inserted into the disc space where the spinal disc is still in place; where at least a portion of the disc has been removed and a distractor is inserted into the disc space and guard 160 is placed over the distractor; or the guard may be inserted into the disc space without first using a distractor.

As shown in FIG. 10, extensions 170, 172 of guard 160 are shaped to penetrate the disc space to help secure guard 160 in position to the spine. Extensions 170, 172 may also be beneficial in spacing apart the vertebral bodies, restoring lordosis, or for correcting a relative translation of the vertebral bodies. After insertion, guard 160 may be, but need not be, further fixated to the spine by the use of one or more fasteners including screws 196, 198, pins, or other suitable elements, preferably into each of the adjacent vertebral bodies. Again, it should be noted that the presence of foot plate 174 is preferred when the guard is used anteriorly but is not essential.

With reference to FIGS. 11 and 12, the correct depth of the disc space to be prepared is determined. The correct disc space depth may be determined in a number of ways. For example, the depth may be determined by pre-operative imaging studies such as plain radiographs, CAT scans, MRIs, and the like. Alternatively, the depth may be determined by direct visualization and/or measurement at the time of surgery, or by intraoperative radiographic monitoring, or any combination of the above. In using radiographic monitoring, for example, a lateral x-ray, the surgeon can assess the depth of the disc space from the length of either or both of extensions 170, 172, and the remaining depth of the disc space. For example, alternatively the surgeon may radiographically monitor the progress of cutter mechanism 104 towards the posterior aspect of the vertebral bodies. Additionally, the surgeon by looking toward the spine through the passage of the guard can assess the bone to be resected prior to resecting any bone. Intraoperative radiographic monitoring will confirm to the surgeon whether the guard is generally parallel to the disc space, the thickness of the bone to be cut, the depth of resection for each of the adjacent vertebral bodies, if the guard is centered from side to side, and the depth of extensions into the space so as to assess the depth of the disc space.

Disc penetrating extensions 170,172 are inserted into the disc space to contact the adjacent end plates of the vertebral bodies and, if not already in the desired position, to position the adjacent vertebral bodies in the appropriate distraction and angular orientation to each other for bone resection. After the adjacent vertebral bodies are in the desired position, guard 160 may be secured to the spine such that foot plate 174 is placed against the anterior aspect of the vertebral bodies and screws 196, 198 are inserted through holes 176, 178 and into the adjacent vertebral bodies. The adjacent vertebral bodies are held in the desired position relative to one another during the bone removal procedure, and if desired, also during the spinal implant insertion procedure.

Figure 13:
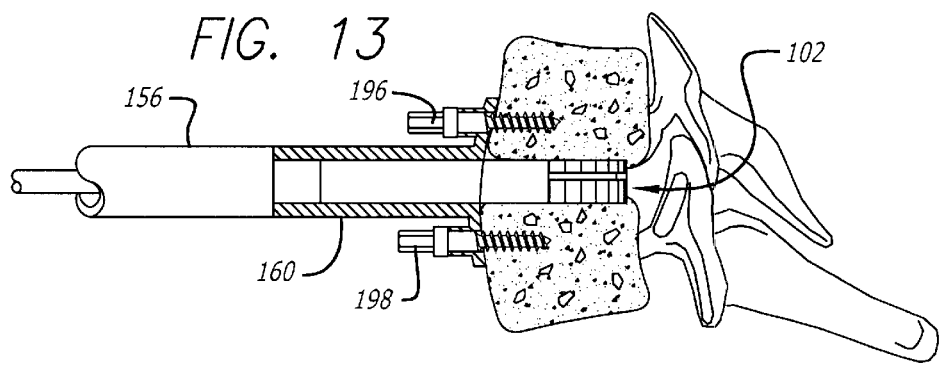
FIG. 13 is a partial side sectional view of two adjacent vertebral bodies with the extended guard of FIG. 11 in partial cross-section installed into the disc space and secured to the adjacent vertebral bodies by installation screws with a bone removal device inserted therein and into the disc space.

Referring to FIG. 13, cutter mechanism 104 is advanced through guard 160 into the disc space, removing bone from each of the adjacent vertebral bodies to the desired depth. It should be noted that the progress of distal end 102 of the cutter instrument towards the posterior aspects of the vertebral bodies may be monitored radiographically for greater accuracy. The desired depth also may be determined with adjustable depth stop 156 that may be set to limit the depth of the cutter insertion. Cutter mechanism 104 is then removed. Debris can be removed by suction and/or irrigation, and optionally with grasping instruments such as rongeurs.

Figure 14:
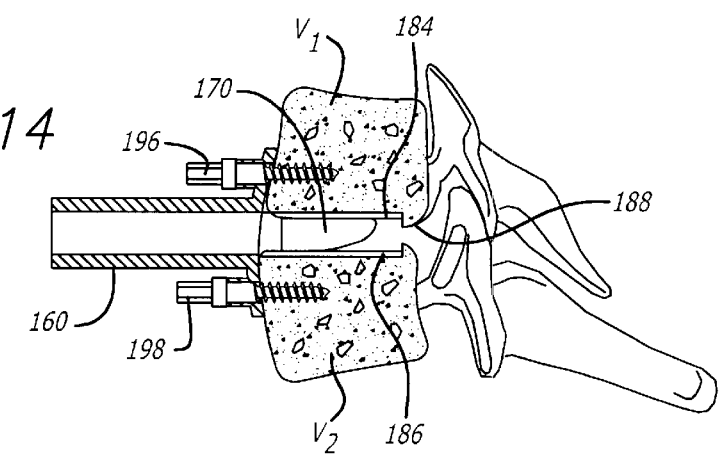
FIG. 14 is a partial side sectional view of two adjacent vertebral bodies with the extended guard in partial section installed into the disc space and secured to the adjacent vertebral bodies by installation screws with the installation space formed across the disc space and into the adjacent vertebral bodies.

FIG. 14 shows a cutaway side view of adjacent vertebral bodies $V_1$ and $V_2$ that have had surfaces 184 and 186 formed in their respective adjacent end plates. The remaining portion of the more dense, bony rim 188 assists in retaining the spinal implant in the desired position between the adjacent vertebral bodies by acting as an abutment preventing lateral or posterior movement of the spinal implant. The prepared faces of these abutment portions of the vertebral end plate also increase the surface area of contact between the spinal implant and the vertebral body. FIG. 14 also shows the cut portion of the disc space being taller than extension 172.

Figure 15:
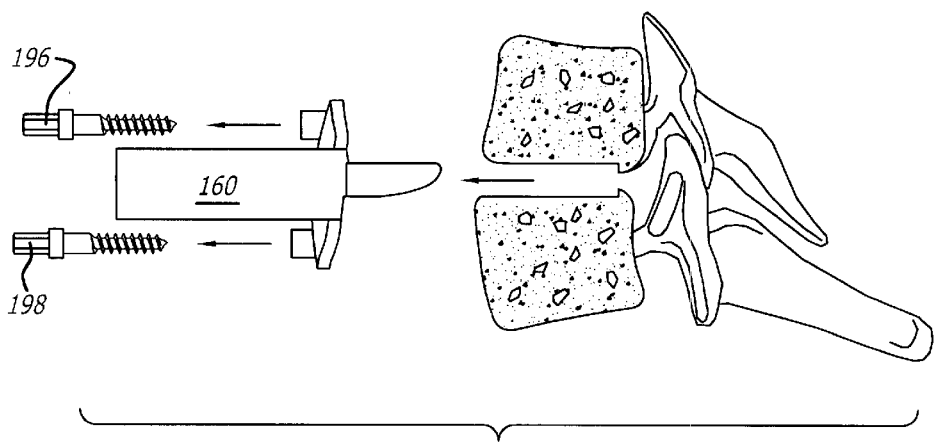
FIG. 15 is a partial side sectional view of two adjacent vertebral bodies with the extended guard of FIG. 11 being removed.

After removal of cutting mechanism 104, the surgeon has two options depending upon whether the cutter thickness and the spinal implant height are similar or not. If the cutter thickness and spinal implant height are not similar, then the surgeon may elect to remove guard 160 as shown in FIG. 15. Next, the correct spinal implant height is determined. This determination may be made by knowing the extent of distraction prior to cutting, or by trialing the space with spacers to determine the correct height, or by distracting the space and measuring the height. Once the implant height has been determined, the correct spinal implant is selected which preferably has a width equal to the space prepared and a length selected to correspond to the depth of the space preparation or less, and a height sufficient to restore appropriate spacing to the inter space. Additionally, the spinal implant is preferably selected to impart a desired amount of lordosis to the vertebral bodies adjacent the interspace.

The spinal implant is then inserted into the prepared space. During insertion, the prepared space may be held at least in part distracted as the spinal implant is introduced into the prepared space. Preferably, the implant is introduced with an implant driver into the spine and advanced along the mid-longitudinal axis of the prepared space to the desired depth by urging it forward as by impaction, and/or pushing it forward, or the equivalent.

If, after removal of cutter mechanism 104, passageway 168 of guard 160 has a height as great as the height of the implant to be inserted, then the surgeon may insert the spinal implant through guard 160. It should be noted that if the guard was selected to have a passageway height greater than the cutter thickness, then the ideal height of the spinal implant may be determined by introducing into the disc space progressively taller spacers to determine the optimal disc space distraction and implant height. After insertion of the implant, the implant driver, if one was used, is removed.

If the implant is to be inserted without the guard, then guard 160 is removed from the adjacent vertebral bodies prior to the insertion of the implant.

Device 100 also may be used in a posterior approach, for example, between the adjacent vertebrae in the lower back, such as $L_1$ through $S_1$, from a posterior approach, or from posterior to the transverse processes of the vertebrae, including both straight posterior and posterolateral. If a posterior approach is used, many of the above steps apply. In order to position guard 160, the dural sac is retracted towards the side opposite of the insertion and protected along with the traversing nerve root. For easier visualization of the area to be resected, guard 160 may include inspection slots placed away from tissues such as the dural sac and nerves that need to be protected. Guard 160 is preferably placed to one side of the midline, that is, the line separating right and left halves of the vertebral bodies, especially when the surgeon intends to place an implant on each side of the midline. During the posterior approach, the surgeon will normally prefer to place two implants, each having a maximum width less than half of the width of the disc space and generally oriented from the back to the front of the disc space, or slightly toed in. Alternatively, the surgeon may elect to place but a single implant. In such instance, the single implant may be placed more diagonally across the disc space allowing for the use of a longer implant, or to place two implants from the same side.

In a posterior lateral approach, no laminar bone need be removed as the disc space is entered lateral to the spinal canal. In that case, two toed-in implants can be used or a single implant placed diagonally which may be longer than when the two are used. As the disc penetrating extensions themselves (the part in the disc) can be of various cross sectional shapes it may be preferred to utilize a distractor having a height greater than its width so that it can be introduced on its side and then rotated 90° to its height. In that case, it is preferred that at least one of the diagonals, if not both, be reduced in length by reduction of the junctions or corners where the top and bottom meet the sides. Alternatively, the trial spacers may resemble the implant in shape, though it may be preferred to leave the bone engaging surfaces smooth to facilitate removing the trial implants or distractors. As used herein, the term trials refers to spacers that are similar to an implant in shape but without a bone engaging surface such that it is smooth and lesser in height than an implant and used to determine the appropriate tension for the disc space in which a spinal implant is to be inserted.

Figure 16:
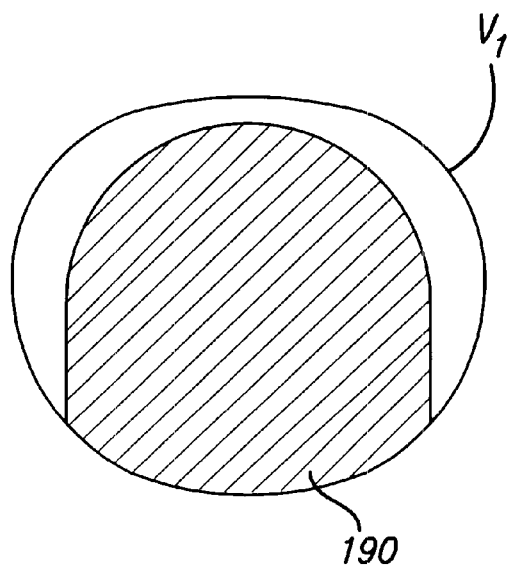
FIG. 16 is a top plan view of an end plate of a lumbar vertebral body with an implantation space formed therein from an anterior approach with the instrumentation and method in accordance with the present invention.
Figure 17:
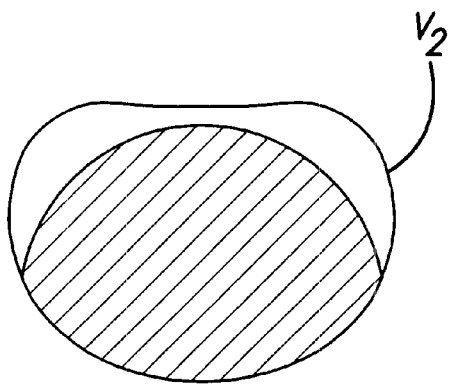
FIG. 17 is a top plan view of an end plate of a cervical vertebral body with an implantation space formed therein from an anterior approach with the instrumentation and method in accordance with the present invention.
Figure 18:
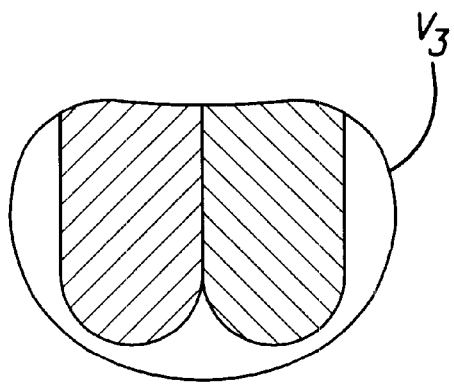
FIG. 18 is a top plan view of an end plate of a lumbar vertebral body with implantation spaces formed therein from a posterior approach with the instrumentation and method in accordance with the present invention.

FIGS. 16–18 illustrate various views of vertebral bodies with implantation spaces that have been prepared by a device incorporating the present invention. The cross-hatching in these figures represents the machined areas of vascular bone. FIG. 16 shows a top view of a first vertebral body $V_1$, such as in the lumbar spine where the depth of resection is sufficient to allow for the full diameter of the cutter to pass into the disc space, leaving parallel straight sides and anatomic contour at the trailing (anterior) aspect of the vertebral body. The created space includes a leading portion adapted to correspond to the leading end of an implant and sides adapted to correspond to at least a portion of the sides of the implant. First vertebral body $V_1$ has a surface 190 formed by working end 110 as shown in FIG. 4. The width of surface 190 formed on first vertebral body $V_1$, closely matches the width of working end 110 that was advanced into the disc space along a single front to back axis.

FIG. 17 shows the top view of a second vertebral body $V_2$ such as in the cervical spine where the depth of resection may be limited such that the full diameter of the cutter never passes into the bone. The created space is adapted to correspond to at least a portion of the leading end of the implant and possibly a portion of the sides.

FIG. 18 shows the top view of a lumbar vertebral body $V_3$ showing side-by-side passes of the hemi-width cutter from a posterior to anterior approach. In such an instance, the cutter preferably has a maximum width of less than half the width of the disc space. The prepared areas may or may not touch each other.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. Apparatus for preparing a space in the human spine to receive an implant between adjacent vertebral bodies, comprising:
    a shaft having a proximal end and a distal end opposite the proximal end;
    a mounting member disposed at the distal end of said shaft;
    a working end having a leading end adapted for insertion into the spine and a trailing end opposite said leading end, said working end mounted on said mounting member, said working end having at least two cutters selected to create a predetermined surface contour into each of the adjacent vertebral bodies as said working end is moved;
    a drive mechanism operably connected to said trailing end of said working end for moving said cutters of said working end; and
    a power source operably connected to said drive mechanism.

2. The apparatus of claim 1, wherein said cutters are adapted to simultaneously create predetermined surface contours on the respective end plates of the adjacent vertebral bodies.

3. The apparatus of claim 1, wherein said cutters include teeth formed thereon to cooperatively engage said drive mechanism, said drive mechanism and said teeth being configured such that said cutters are rotated by said drive mechanism.

4. The apparatus of claim 1, wherein a first and a second of said cutters are adapted to be rotated in opposite directions by said drive mechanism.

5. The apparatus of claim 1, wherein said working end has at least a top cutter and a bottom cutter.

6. The apparatus of claim 1, wherein said working end is convex.

7. The apparatus of claim 1, wherein said working end is tapered outwardly from a front surface of said working end.

8. The apparatus of claim 1, wherein said working end includes a leading edge configured as a bone-cutting surface.

9. The apparatus of claim 1, wherein at least at least one of said cutters has a width, said width substantially matches the width of the nucleus pulposus of a disc space in which it is inserted.

10. The apparatus of claim 1, wherein at least one of said cutters is substantially planar.

11. The apparatus of claim 1, wherein at least one said cutter cutters configured such that it is generally parallel to said surface contour formed in the vertebral body as said working end is moved by said drive mechanism.

12. The apparatus of claim 1, wherein said working end includes outwardly facing first and second cutters, and said first and second cutters are inclined relative to one another.

13. The apparatus of claim 1, wherein said working end is detachable from said mounting member.

14. The apparatus of claim 1, further comprising:
    a guide having an opening for providing protected access to the adjacent vertebral bodies and a disc space therebetween, said opening being configured for passage of said working end through said guide.

15. The apparatus of claim 1, wherein said working end is driven in a reciprocating, arcuate motion by said drive mechanism.

16. The apparatus of claim 1, wherein said working end includes a wheel having cutter teeth along its perimeter.

17. The apparatus of claim 1, wherein said drive mechanism is adapted to produce a rotary movement of said working end about an axis generally perpendicular to a longitudinal axis of said shaft and a general plane of the vertebral end plate.

18. The apparatus of claim 1, wherein said drive mechanism is adapted to produce one of an oscillating rotation and a vibratory motion of the working end.

19. The apparatus of claim 1, wherein said drive mechanism comprises a gas-driven turbine powered by a source of compressed gas.

20. The apparatus of claim 1 wherein said drive mechanism is operable to move said working end in at least two degrees of freedom.

21. The apparatus of claim 1, further comprising a suction mechanism for removing bits of debris created by said cutter of said working end.

22. The apparatus of claim 1, further comprising an irrigation channel configured through said shaft for delivering irrigation fluid to the surgical site.

23. The apparatus of claim 1, further comprising at least one stop member to limit the depth of travel of said working end into the spine.

24. The apparatus of claim 1, further comprising:
    a guide having an opening for providing protected access to the adjacent vertebral bodies and a disc space therebetween, said opening being configured for passage of said working end through said guide; and
    first and second disc penetrating extensions extending from said guide for insertion into the disc space between the adjacent vertebral bodies, each of said disc penetrating extensions having a portion for bearing against each of the adjacent end plates of the adjacent vertebral bodies, each of said portions of said disc penetrating extensions having an upper surface adapted to contact one of the adjacent end plates of the adjacent vertebral bodies and a lower surface adapted to contact the other of the adjacent end plates of the adjacent vertebral bodies, said portions of said disc penetrating extensions having a height between said upper and lower surfaces and a length sufficient to properly align and distance apart the adjacent vertebral bodies.

25. The apparatus of claim 24, wherein said upper and lower surfaces are parallel to each other along a substantial portion of the length thereof.

26. The apparatus of claim 24, wherein said guide has an external surface at its distal end and said disc penetrating extensions are at least in part coextensive with said external surface.

27. The apparatus of claim 24, wherein said disc penetrating extensions are diametrically opposed to each other and spaced apart from one another to provide access to the adjacent vertebral bodies from within the disc space.

28. The apparatus of claim 24, wherein the height of said disc penetrating extensions have at least a portion that approximates the height of a normal disc space between the adjacent vertebral bodies.

29. The apparatus of claim 24, wherein said disc penetrating extensions have a tapered leading end to facilitate placement of said disc penetrating extensions into the disc space, said portion of said disc penetrating extensions having opposite surfaces for bearing against the end plates of the adjacent vertebral bodies, said opposite surfaces diverging sway from said guide along at least a portion of their length.

30. The apparatus of claim 24, wherein said upper and lower surfaces converge away from said guide along at least a portion of their length.

31. The apparatus of claim 24, wherein said guide conforms at least in part to the exterior surface of the adjacent vertebral bodies.

32. The apparatus of claim 24, further comprising means for penetrating the two adjacent vertebral bodies.

33. The apparatus of claim 24, wherein said disc penetrating extension has a length greater than one-half the depth of the disc space measured from the anterior aspect to the posterior aspect of the disc space.

34. The apparatus of claim 24, wherein said guide has an interior having a cooperating surface for guiding a corresponding cooperating surface on said mounting member.

35. The apparatus of claim 1, in combination with an implant sized and shaped to match the space formed in the spine by said working end.

36. The combination of claim 35, wherein said implant is one of a spinal implant and a spacer.

37. The combination of claim 35, further in combination with an implant driver configured to cooperatively engage said implant to insert said implant into the spine.

38. The apparatus of claim 1, in combination with a distractor for spacing apart the adjacent vertebral bodies.

39. The apparatus of claim 1, wherein at least a portion of said cutters are separated by a space and substantially overlie one another, said drive mechanism being configured to engage said cutters outside the space separating said cutters.

* * * * *

UNITED STATES PATENT AND TRADEMARK OFFICE
CERTIFICATE OF CORRECTION

PATENT NO.    : 6,692,501 B2
DATED         : February 17, 2004
INVENTOR(S)   : Gary K. Michelson It is certified that error appears in the above-identified patent and that said Letters Patent is hereby corrected as shown below:

Title page,
Item [60], Related U.S. Application Data, "2000," should be -- 2000. --

Column 15,
Line 64, change "at least at least one" to -- at least one --.

Column 16,
Line 3, after "one" insert -- of --; and
Line 4, change "cutter cutters" to -- cutters is --.

Signed and Sealed this

Eighth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,692,501 B2
DATED        : February 17, 2004
INVENTOR(S)  : Gary K. Michelson It is certified that error appears in the above-identified patent and that said Letters Patent is hereby corrected as shown below:

Title page,
Item [60], Related U.S. Application Data, "2000," should be -- 2000. --; and delete "and provisional application No. 60/238,255, filed on Oct. 5, 2000."

Column 15,
Line 64, change "at least at least one" to -- at least one --.

Column 16,
Line 3, after "one" insert -- of --; and
Line 4, change "cutter cutters" to -- cutters is --.

This certificate supersedes Certificate of Correction issued June 8, 2004.

Signed and Sealed this

Twentieth Day of July, 2004

JON W. DUDAS
*Acting Director of the United States Patent and Trademark Office*